United States Patent
Marin Cruz et al.

(10) Patent No.: US 10,676,829 B2
(45) Date of Patent: Jun. 9, 2020

(54) CORROSION INHIBITION COMPOSITION FOR PIPELINES, PROCESS OF ELABORATION AND SYNTHESIS

(71) Applicant: INSTITUTO MEXICANO DEL PETROLEO, Mexico City (MX)

(72) Inventors: Jesus Marin Cruz, Mexico City (MX); Araceli Vega Paz, Mexico City (MX); Luisa Elena Montiel Sanchez, Mexico City (MX); Salvador Castillo Cervantes, Mexico City (MX); Rafael Martinez Palou, Mexico City (MX); Arquimedes Estrada Martinez, Mexico City (MX); Luis Manuel Quej Ake, Mexico City (MX); Jose Luis Rodolfo Benitez Aguilar, Mexico City (MX); Veronica Sanchez Garcia, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 163 days.

(21) Appl. No.: 15/981,947

(22) Filed: May 17, 2018

(65) Prior Publication Data

US 2018/0265991 A1    Sep. 20, 2018

Related U.S. Application Data

(62) Division of application No. 14/526,152, filed on Oct. 28, 2014, now Pat. No. 10,011,908.

(30) Foreign Application Priority Data

Oct. 29, 2013    (MX) .......................... A/2013/012611

(51) Int. Cl.
| | | |
|---|---|---|
| C23F 11/14 | (2006.01) |
| C07D 233/64 | (2006.01) |
| C07D 249/18 | (2006.01) |
| C07D 233/58 | (2006.01) |
| C09K 8/54 | (2006.01) |
| F17D 1/08 | (2006.01) |
| F17D 3/12 | (2006.01) |

(52) U.S. Cl.
CPC .......... *C23F 11/149* (2013.01); *C07D 233/58* (2013.01); *C07D 233/64* (2013.01); *C07D 249/18* (2013.01); *C09K 8/54* (2013.01); *C23F 11/141* (2013.01); *F17D 1/08* (2013.01); *F17D 3/12* (2013.01)

(58) Field of Classification Search
CPC ...................................................... C23F 11/149
See application file for complete search history.

(56) References Cited

U.S. PATENT DOCUMENTS

| | | |
|---|---|---|
| 6,350,721 B1 | 2/2002 | Fu et al. |
| 7,057,050 B2 | 6/2006 | Meyer |
| 7,160,507 B2 | 1/2007 | Dahlmann et al. |
| 2008/0200357 A1 | 8/2008 | Chasan et al. |
| 2009/0220689 A1 | 9/2009 | Bahls |
| 2010/0084612 A1 | 4/2010 | Acosta et al. |
| 2010/0291307 A1 | 11/2010 | McGee et al. |
| 2012/0021957 A1 | 1/2012 | Alemany et al. |

FOREIGN PATENT DOCUMENTS

| | | |
|---|---|---|
| WO | 2008/091429 | 7/2008 |
| WO | 2008/157234 | 12/2008 |
| WO | 2010/128313 | 11/2010 |
| WO | 2011/000895 | 1/2011 |
| WO | 2012/028542 | 3/2012 |

*Primary Examiner* — Donald R Spamer
(74) *Attorney, Agent, or Firm* — Dickinson Wright PLLC

(57) ABSTRACT

Compounds and compositions are used as corrosion inhibitors for pipelines for crude oil containing water with high salt concentrations. The inhibitors are ionic liquids, imidazoles, benzotriazoles, and mixtures thereof. The composition includes two or more members of the inhibitors with a solvent. The inhibitors reduce corrosion of metallic surfaces of the pipelines containing crude oil having 0.2 and 40 wt % water, 10,000 to 70,000 ppm salt, and 9 to 600 ppm hydrogen sulfide. A synergic effect is provided by two or more different inhibitors. This synergy is derived from interactions with the metallic surface, among themselves or with the corrosive medium depending on the chain length, to inhibit the corrosion with decrease of the formulation dose. The composition can be a ternary formulation of the three families or two components of one family and a third component of a different family.

21 Claims, 1 Drawing Sheet

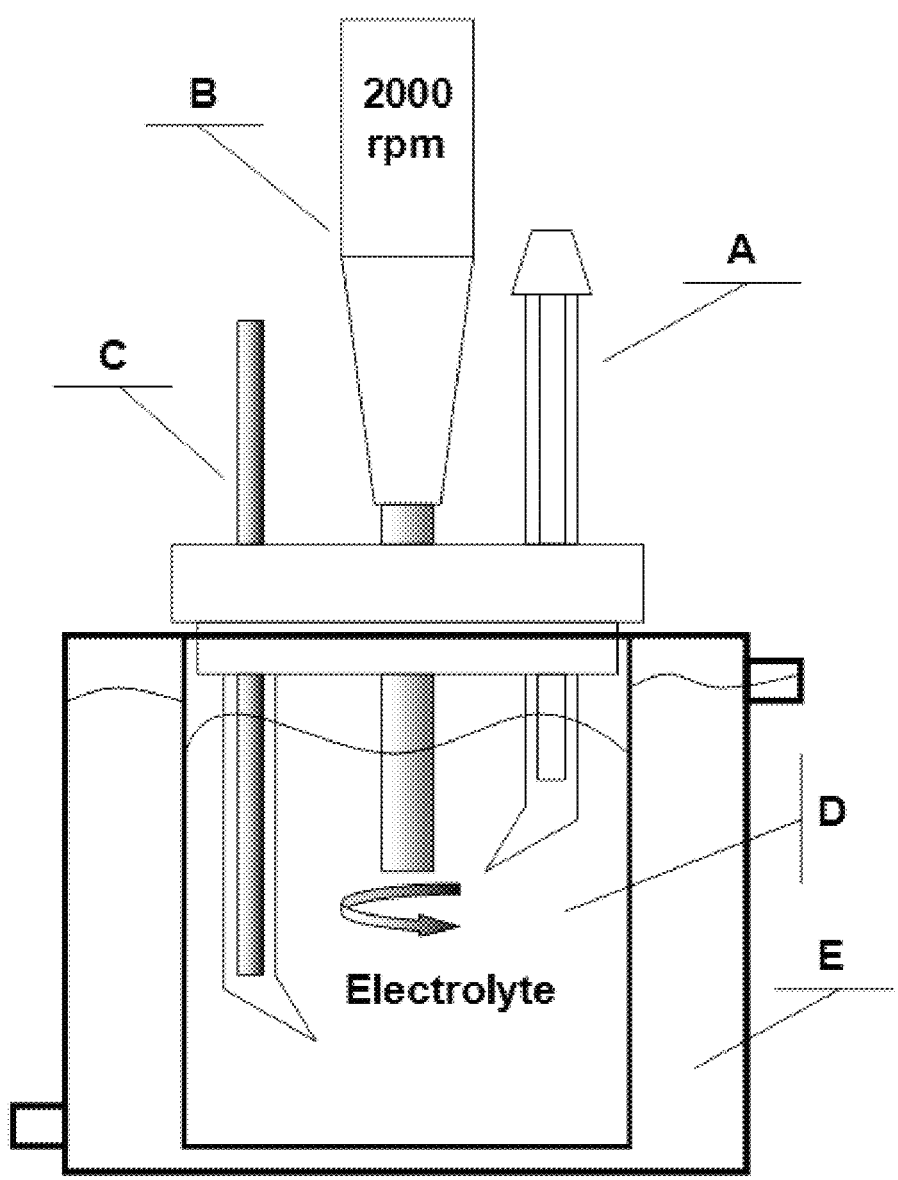

CORROSION INHIBITION COMPOSITION FOR PIPELINES, PROCESS OF ELABORATION AND SYNTHESIS

CROSS-REFERENCE TO RELATED APPLICATION

This application is a divisional application of U.S. Ser. No. 14/526,152 filed Oct. 28, 2014, which is hereby incorporated by reference in its entirety. This application also claims the benefit of and priority to under 35 U.S.C. § 119 to Mexican Patent Application No. MX/a/2013/012611 with a filing date of Oct. 29, 2013, the disclosure of which is incorporated herein by reference in its entirety.

FIELD OF THE INVENTION

The present invention relates to the synthesis of basic compounds, the preparation of compositions and its application as corrosion inhibitors for pipelines that transport, besides of crude oil, associated congenital water containing high salt concentrations; the inhibitors are basically constituted by compounds of molecular structure families such as: imidazoles, benzotriazoles and ionic liquids; said formulations can include two or more components of each family and can use as alcohol solvents, xylene, toluene or mixtures thereof.

The inhibitors object of the present invention control the corrosion of metallic surfaces of the pipelines containing concentrations of congenital water from 0.2 up to 40% by weight, salt concentration between 10,000 and 70,000 ppm and concentration of hydrogen sulfide between 0 and 600 ppm, by means of the synergic effect between two or more components of the same family, or two or more different molecular structure families; this synergy is derived from its interactions with the metallic surface, among themselves or with the corrosive medium itself due to its chemical, physical and transportation properties, based on the length of the involved chain, that improves corrosion control achieving the simultaneous decrease of dosing of formulations. Whereas, the ternary formulations use a component of each one of the three families or two components of the same family and a third component belonging to the second family of molecules. In all cases, the formulations can include solvents as xylene, methanol and toluene, or a mixture of two or three of them.

The application of these compounds and formulations is focused, but not limited to its use as corrosion inhibitors in typical transportation environments of crude oil and petroleum industry generally.

BACKGROUND OF THE INVENTION

Corrosion inhibitors are compounds or formulations of chemical compounds wherein the active part blocks or modifies the electronic transfer process, responsible of the corrosion phenomena, between the metallic surface and the surrounding medium. In the petroleum industry, its use is generalized to control metal corrosion in a wide variety of mediums and conditions. Independently of the system, the interaction between the active component and the metallic surface plays a determining role in its development and consequently in the corrosion control; said interaction depends on the chemical properties of the active compound depending on its molecular structure, on physical and chemical properties of the metal and its own interaction with the surrounding medium; furthermore, of the operation conditions such as system pressure, temperature and hydrodynamics.

In the particular case of pipes for the transportation of crude oil (pipelines), the control of the internal corrosion is complicated mainly by the frequent variations present in the type of the transported crude, as well as in the water, salts and dissolved gases contents; nevertheless, the use of inhibitors is still the more profitable alternative to face it.

Among the main chemical families that have been used to inhibit corrosion in pipelines are nitrogenous compounds such as ammonium quaternary salts, amines, amides and including amino acids; particularly the use of fat imidazolines and fat amines as corrosion inhibitors in the petroleum industry is well known. Generally, it is accepted that these compounds work upon absorption forming a protecting film over the metallic surface; nevertheless, independent of the inhibitor used, these also have limitations.

In the literature that mentions the use of corrosion inhibitors with specific application for hydrocarbons transport, are the following international patents:

U.S. Pat. No. 7,057,050 refers to the preparation of novel corrosion inhibitors imidazoline base and its use to inhibit corrosion in metallic flow lines. According to the patent, the inhibitors are a series of new corrosion inhibitors based on imidazoline base substituted with acrylates, of the following formula:

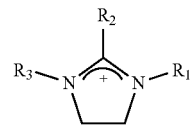

Wherein $R_1$ is an alkyl radical having from 2 to 8 carbon atoms; $R_2$ is a radical derived from a fatty acid, and $R_3$ is a radical derived from an unsaturated acid.

U.S. Pat. No. 7,160,507 relates to an additive and a method of corrosion inhibition on devices used for the recovery, transportation and processing of crude oil; the inhibitor comprises an alkoxylated quaternary compound of the formula:

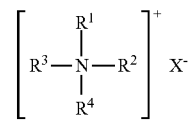

where $R_1$ and $R_2$ are independently groups of the formula-(B)-(O-A)$_n$-O—CO—$R_5$ or-(A-O)$_n$-(C)—CO—O—$R_5$; $R_3$ is $C_1$-to $C_{30}$-alkyl or $C_2$ to $C_{30}$-alkenyl; $R_4$ is an organic radical with 1 to 100 atoms optionally containing heteroatoms; $R_5$ is an alkyl or an alkenyl; n is a number from 1 to 20; A is an alkylene group; B is an alkylene group, C is a $C_1$-to $C_{30}$-alkylene and X is an anion.

In patent application US $C_{084612}$ A1, a method for inhibiting corrosion in metallic surfaces used in manufacture, transportation, storage and separation of crude oil and gas is described; the method comprises adding the fluid a sufficient quantity of a synergist, when $H_2S$ is present in the fluid, or no synergist when $H_2S$ is present in the fluid and a composition comprising the following formula and salts thereof:

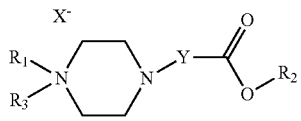

Wherein $R_1$ and $R_3$, $C_nH_{2n+1}$ wherein n=0 to 12; benzyl; or H. $R_2$ is a $C_1$ to $C_{22}$ alkyl. X— is a halogen or a carboxylate and is only present when $R_1$ and $R_3$ are present. Y is $(CH_2)_n$ with n=1 to 8 and wherein $R_3$ and $R_1$ cannot be hydrogen at the same time.

Another structure mentioned in this patent application is:

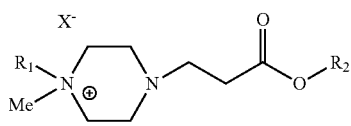

wherein $R_1$ and $R_2$ are similar to the above structure and is $C_nH_{2n+1}$ wherein n=0 is a $C_1$ to $C_{22}$ alkyl. X—=Cl, Br or I.

WO 157234 relates to novel quaternary-nitrogen compounds in its structure and formulations used by these compounds that are useful as corrosion inhibitors in the gas and petroleum industry. The quaternary nitrogen-containing corrosion inhibitors have the following formula:

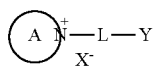

Wherein:

is an aromatic, nitrogen-containing ring of 5 to 14 atoms, optionally containing an additional N, O or S ring atom in the additional N ring or can be substituted with one or more alkyl, alkenyl, aryl, arylalkyl, cycloalkyl, amine, aminoalkyl, alkoxy, hydroxyalkyl or cyano groups, or a mixture thereof; Y is a group of formula —OC(O)$R_1$; L is an $C_1$-$C_{10}$ alkyl, $C_2$-$C_{20}$ alkenyl of the formula —$CH_2CH(OR_2)$$CH_2$—; $R_1$ is $C_8$-$C_{20}$ alkenyl; $R_2$ is H or —C(O)$R_1$; $R_3$ and $R_4$ are independently selected from H, alkyl, alkenyl, amino, aminoalkyl, alkoxy, hydroxyalkyl or cyano; and X is Br, Cl or I.

WO 091429 relates to corrosion inhibition in ferrous and non-ferrous metals in aqueous-based environments by the use of formulations that use at least two mercaptan compounds of the following formulae:

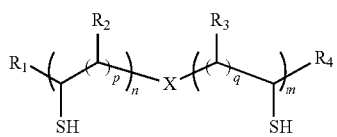

wherein X is C, N, O or S; $R_1$, $R_2$, $R_3$ y $R_4$ are independently H or methyl; n and m are independently integers from 1 to 5 and p and q are independently integers from 1 to 4.

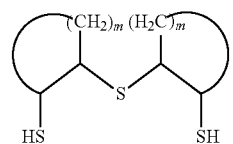

wherein m is an integer from 3 to 4; and

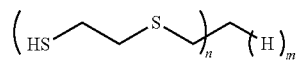

wherein m is an integer from 1 to 4; and n=4−m.

WO 128313 relates to a corrosion inhibitor for use in the oil and gas exploration, recovery and processing industries consisting of a quaternary ammonium compound of the formula:

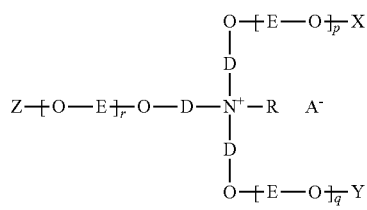

wherein R is $C_1$-6 alkyl, $C_2$-6 alkenyl, aryl, arylalkyl; X, Y and Z are each independently H or $R_1CO$— group, provided that at least one of X, Y, Z is $R_1CO$— where $R_1$ is a $C_{5-23}$ alkyl or alkenyl containing 0, 1, 2, or 3 double bounds; D is $C_{2-6}$ alkylene; E is $C_{2-4}$ alkylene; p, q and r are independently integers from 0 to 20, with the proviso that p+q+r=3 to 20; and A is an anion.

Other patent applications related to corrosion inhibitors with application in crude oil transportation are patent application WO 000895 that refers to a polymeric product obtained by the reaction between alkoxylated fat amine and a dicarboxylic acid derivative, whereas patent application WO 028542 refers to the use of polyamine polyester compounds and polyquaternary polyester ammonium as corrosion inhibitors in the transportation of crude oil and in the oil and gas wells.

BRIEF DESCRIPTION OF THE DRAWINGS

In order to clearly understand the evaluation of the synthesis of individual chemical structures; as well as the evaluation of the inhibition efficiency to corrosion of the corrosion inhibition formulation, object of the current invention is made to the FIGURE attached without limiting the scope of the invention:

FIG. 1 illustrates the electrochemical cell used in the evaluation of corrosion inhibition evaluation.

DETAILED DESCRIPTION OF THE INVENTION

The present invention is directed to synthetizing individual chemical compounds and providing corrosion inhibitor compositions formulated from synthesized structures that belong to different chemical families: imidazoles, benzotriazoles and ionic liquids. The basic criteria for the design of said formulations is based on the knowledge of the effect that has a particular structure over the modification of involved phenomena in the corrosion process and synergy that is generated using together with one or more molecular structures belonging to a particular family, in this case the difference is mainly centered on the chain length or on structures belonging to one or more different families, situation where the inherent functionality to each compound family is taken advantage. The procedure for obtaining each formulation comprises the following steps: a synthesis step of the structures used as an active component; a step of incorporation of one, two or three active components of the same or different chemical structure family; a step of incorporation of the solvent and a step of stirring to obtain the complete integration of the formulation.

The composition object of the current invention are useful to control the internal corrosion in pipelines transporting crude oil wherein the content of associated water is from 0.2 to 40% by weight and the concentration of inorganic salts (i.e. chlorides, sulfates, carbonates, among others) ranges from 10,000 and 70,000 ppm and wherein there is evidence of the presence of $H_2S$ and $O_2$, as dissolved gases. The crude oil can include the corrosion inhibiting compounds in an amount of 50 to 2500 mg/L. In one embodiment, the crude oil contains the corrosion inhibiting compounds in an amount of 500 to 2500 mg/L.

Two of the families of the compounds involved in the current invention belong to azoles and are mainly amine derivatives of imidazole and benzotriazole whereas the third belongs to ionic liquids; the structural characteristics of each family is described below:

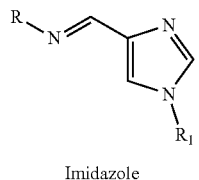

Imidazole

Wherein R is a saturated or unsaturated hydrophobic hydrocarbon chain containing 2 to 25 carbon atoms and can be linear or branched. The chain can be an alkyl.

$R_1$ is hydrogen or a linear or branched alkyl radical containing from 1 to 5 carbon atoms.

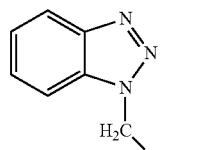

Benzotriazole

Wherein R is a saturated or unsaturated hydrophobic hydrocarbon chain containing 2 to 25 carbon atoms and can be linear or branched, inclusively it can have internal substituents that increase its corrosion inhibition properties of the original structure. Examples of internal substituents are the amide and amine groups

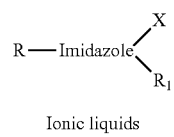

Ionic liquids

Wherein R is a saturated or unsaturated hydrophobic hydrocarbon chain containing 2 to 25 carbon atoms and can be linear or branched.

$R_1$ is hydrogen or a linear or branched alkyl radical containing from 1 to 5 carbon atoms; X is a halogen, preferably Cl, Br or I.

This invention also considers the compositions where compounds from the imidazoles, benzotriazoles and ionic liquid families are involved; these mixtures result in a binary or tertiary combination among members of the same or different families.

In the case of binary mixtures of the same families, the current invention refers to, but is not limited to, the following cases:

Formulations composed by the members of the imidazole amine derivatives family, family A, with general formula

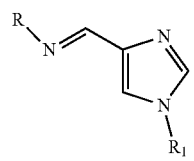

Wherein, for the first member of the composition, component A1, R is a saturated or unsaturated hydrophobic hydrocarbon chain containing from 2 to 10 carbon atoms but preferably from 4 to 8 carbon atoms; whereas for the second member of the composition, component A2, R is a saturated or unsaturated hydrophobic hydrocarbon chain containing from 11 to 25 carbon atoms, more preferably from 12 to 20 carbon atoms. In both cases, the hydrophobic hydrocarbon chain can be linear or branched and $R_1$ is, also for both members, a hydrogen or a linear or branched alkyl radical containing from 1 to 5 carbon atoms. The imidazole forms the cation and the Cl, Br and I form the anion.

The compositions are mixtures of components A1 and A2 with a ratio that can be of 1:1, 1:2, 1:3, 3:1, 2:1.

Formulations composed by two members of amine derivatives of the benzotriazole family, family B, with general formula

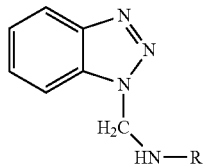

Wherein, for the first member of the composition, component 81, R is a saturated or unsaturated hydrophobic hydrocarbon chain containing from 2 to 10 carbon atoms, but preferably from 6 to 10 carbon atoms and it can be linear or branched or inclusively can have internal substituents that increase the corrosion inhibition properties of the original structure; whereas, for the second member of the composition, component B2, R is a saturated or unsaturated hydrophobic hydrocarbon chain containing from 11 to 25, but preferably from 14 to 18 carbon atoms and can be linear or branched and inclusively can have internal substituents that increase corrosion inhibition properties of the original structure. Examples of internal substituents are the amide and amine groups.

The compositions are mixtures of components B1 and B2 with a ratio that can be of 1:1, 1:2, 1:3, 3:1, 2:1.

Formulations composed by two members of amine derivatives from the ionic liquid family, family C, with general formula

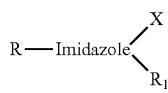

Wherein, for the first member of the composition, component C1, R is a saturated or unsaturated hydrophobic hydrocarbon chain containing from 2 to 10, but preferably from 4 to 8 carbon atoms and can be linear or branched; whereas for the second member of the composition, component C2, R is a saturated or unsaturated hydrophobic hydrocarbon chain containing from 11 to 25, but preferably from 14 to 18 carbon atoms and it can be linear or branched.

For both components, $R_1$ is hydrogen or a linear or branched alkyl radical containing from 1 to 5 carbon atoms and X is halogen, preferably Cl, Br or I.

The compositions are mixtures of components B1 and B2 with a relation that can be of 1:1, 1:2, 1:3, 3:1 and 2:1.

In case of binary mixtures of different families, the current invention refers to, but is not limited to the following cases:

Formulations composed by members of amine derivatives from the imidazole and benzotriazole families.

The compositions are mixtures of the components A1 and B1; A1 and B2; A2 and B1 and A2 and B2, but preferably A2 and B1, with the ratio from 1:3 to 3:1.

Formulations composed by members of amine derivatives from the imidazole and ionic liquid families.

The compositions are mixtures of the components A1 and C1; A1 and C2; A2 and C1 and A2 and C2, but preferably A2 and C1, with the ratio from 1:3 to 3:1.

Formulations composed by members of amine derivatives from the benzotriazoles and ionic liquid families.

The compositions are mixtures of the components B1 and C1; B1 and C2; B2 and C1 and B2 and C2, but preferably B2 and C2, with the ratio from 1:3 to 3:1.

In the case of ternary mixtures of molecules belonging to the same or different families, the current invention refers to, but is not limited to the following cases:

The compositions are mixtures of the following components A1, B1 and C1; A1, B1 and C2; A1, B2 and C1; A1, B2 and C2; A2, B1 and C1; A2, B1 and C2; A2, B2 and C1; A2, B2 and C2; A1, A2 and B1; A1, A2 and B2; A1, A2 and C1; A1, A2 and C2; B1, B2 and A1; B1, B2 and A2; B1, B2 and C1; B1, B2 and C2; C1, C2 and A1; C1, C2 and A2; C1, C2 and B1; and C1, C2 and B2, but preferably A1, A2 and C1; A1, A2 and C2 and B1, B2 and C1 and B1, B2 and C2, with molar ratio from 1:1:1 to 2:1:1, 1:2:1, 1:1:2.

EXAMPLES

Below are described examples of the synthesis of basic structures belonging to the three families involved in corrosion inhibitor formulations and examples of binary and ternary formulations; as well as the evaluation of corrosion inhibition efficiency of the formulations and the individual components.

Example 1

Synthesis of Imidazole Amine Derivatives

Synthesis of N-[1H-imidazole-(4-methylidene)]-hexane-1-amine

In a ball flask attached to a cooler with magnetic stirring, are placed 25 g of 4-imidazolcarboxaldehyde and 20 mL of methanol (MeOH) are added, are maintained in moderated stirring up to full dissolution; 32.5 mL of hexylamine are added, maintaining stirring and 15 additional mL of MeOH are added.

The reaction mixture is maintained under reflux for 9 hours at a temperature of 60° C., between the fourth and the sixth reflux hours; a Dean-Stark trap is placed to withdraw the $H_2O$ generated during the reaction.

Once concluded the reaction time, it is left at room temperature and the solvent is evaporated at reduced pressure. The obtained product is yellow oil with a performance of 81%.

Example 2

Synthesis of N-[1H-imidazole-(4-methylidene)]-decan-1-amine

The same procedure described in Example 1 is followed, using 25 mL of decylamine instead of hexylamine.

The obtained performance in this case is of 78%.

Example 3

Synthesis of Benzotriazole Amine Derivatives

Synthesis of N-(1H-benzotriazole-1-methyl)-octadecan-1-amine

In a ball flask equipped with magnetic stirring, 17.5 g of 1H-Benzotriazole are placed maintaining a moderate stirring, 60 mL of methanol (MeOH) are added and stirring is continued for dissolution. 40 g of 1-octadecylamine are added, stirring is maintained to obtain a slightly yellow crystalline solution and 20 mL of formaldehyde aqueous solution are added.

The mixture is maintained under stirring at room temperature during 2 hours; the reaction product precipitates as a soft solid, the solvent is removed by filtration and is dried at a temperature of 110° C. during 2 h. The performance is of 79%.

Example 4

Synthesis of N-(1H-benzotriazole-1-methyl)-hexane-1-amine

The same procedure of the Example 3 is followed, using 25 mL of 1-hexylamine instead of 1-octadecylamine.

The product is viscous yellow oil with a performance of 89%.

Example 5

Synthesis of Ionic Liquids

Synthesis of 1-allyl-3-methylimidazolium bromide

In a 100 mL ball flask attached to a cooler and with magnetic stirring, 15 g of methylimidazolium dissolved of 25 mL of toluene are added; with the help of an addition funnel; 30 g of allyl bromide are incorporated, the reaction mixture is stirred and is taken at a temperature of 60° C., stirring is maintained for 1.0 hour.

The reaction mixture is washed twice with 10 mL of ethyl acetate and furthermore with 15 mL of ether. The solvent is removed with a Rotavapor®.

The obtained product is dried at high vacuum, obtaining a yellow liquid with a performance of 92%.

Example 6

Synthesis of 1-decyl-3-methylimidazolium bromide

The same procedure described in Example 5 is used, but with the following reagents and quantities:
12 g of methylimidazolium
35 mL of toluene
22 g of bromodecane The reaction mixture is stirred and is taken to a temperature of 95° C. and is maintained under stirring for 2 hours.

The following steps are similar to those of Example 5. An amber liquid with a performance of 87.5% is obtained.

Example 7

Evaluation of Corrosion Inhibiting Properties of Individual Structures and Binary Formulations Object of the Current Invention Methodology of Evaluation
Evaluation Using Electrochemical Impedance Spectroscopy (EIS)

The evaluation of corrosion inhibiting properties of the individual structures and binary compositions was carried out in a conventional electrochemical cell (E) with a three electrode arrangement as the one shown in FIG. 1. This cell allows maintaining stirring and constant temperature during development of measurement.

The inhibiting formulations to be evaluated are added in the desired concentration in the test solution (D), whereas a stirring of 2000 rpm and a temperature of 40° C. are maintained. Furthermore, it is submerged in a sample as a steel disk to the carbon previously destroyed with a 600 sandpaper, this sample has the function of a work electrode (B) in the electrochemical cell; the graphite auxiliary counter electrode (C) and the calomel saturated electrode (A) are placed as reference. The system is maintained under stirring and constant temperature for 3 hours.

After 3 hours, the electrochemical impedance spectrum is obtained in a range of 10 kHz and 10 mHz frequency and the resistance related to corrosion and together with that obtained in an identical experiment but only with the test solution was obtained from this spectrum; the corrosion inhibition efficiency was calculated.

Evaluation of Behavior Tests

The binary and ternary compositions were evaluated through the following behavior tests, specific for this type of product:

Behavior Test NACE ID 182

Method of the Wheel

A sample of carbon steel to API 5L X52 with dimensions of 2.54 cm×1.27 cm×0.025 are weighed and a bottle with 180 mL of test solution is placed, preferably a sample of the system where the inhibitor will be used, or an aggressive saline solution that simulates the acid, basic and neutral environments of the petroleum industry and a specific concentration of the corrosion inhibitor to be evaluated. The bottle is sealed and introduced in a temperature chamber with a 58.4 cm diameter wheel, provided with adequate and sufficient housing for 52 samples (bottles), the temperature of the chamber is increased at the desired value that preferably corresponds to the system operation temperature where the inhibitor is applied; the wheel rotation of 30 revolutions per minute was started during the heating process, that is maintained for a 24 hours period once the temperature is achieved.

At the end of the test, the sample is removed and washed consecutively with hexane, acetone, water, an inhibited solution of hydrochloric acid, a 5% potassium bicarbonate solution, is cleaned with water and soap using a plastic firm bristle swab, is rinsed with deionized water, is washed with acetone and is dried in an oven at 60° C. for one hour, the sample is left to achieve room temperature and is weighed. With the difference of weight obtained in the sample in experiments without (blank) and with inhibitor, the corrosion inhibition efficiency was calculated.

Behavior Test ASTM G 185

Rotating Cylinder, Rp/Weight Loss

A cylindrical carbon steel specimen API 5L X52 with dimensions of 0.793 cm in radius and 1 cm long, is introduced into the electrochemical cell, as the one shown in FIG. 1 where previously the test solution was introduced, that would preferably correspond to a real sample of the system in which the inhibitor will be used and a known concentration of the inhibitor to evaluate. Rotation and temperature conditions are established depending on the system conditions in which the inhibitor will be used and the corrosion inhibition efficiency is evaluated related to the blank experiment (absence of inhibitor) according to the standards ASTM D G 1, ASTM D G 3, ASTM D G 5 y ASTM D G 59.

Similar to the method of the wheel, the corrosion inhibition efficiency can be evaluated by weight loss registering the initial weight of the cylindrical specimen and its weight after the before-mentioned cleaning procedure.

Table 1 shows the characterization of the waters used as test solutions in the evaluation that were carried out both with independent structures and different formulations; whereas Table 2, shows some corrosion inhibitor results obtained with different concentrations of structures belonging to the three families, evaluated as the water identified as SP1 in Table 1.

TABLE 1

Characterization of real samples of water related to the crude transported in pipelines, these samples were used as test solutions in various evaluations of corrosion inhibition properties of the synthetized structures and formulations obtained thereof.

| Analyte, mg/L | Test solution | | |
|---|---|---|---|
| | SP1 | SP2 | SP3 |
| Na | 30,000 | 9,907 | Specification ASTM-D 1141 "Substitute Ocean Water" + 600 mg/L $H_2S$ |
| K | 3,445 | 117 | |
| Ca | 1,980 | 118 | |
| Mg | 1,245 | 32 | |
| Mn | 6.25 | 0 | |
| Sr | 1,388 | 41 | |
| Ba | 52.1 | 0.53 | Specification ASTM-D 1141 "Substitute Ocean Water" + 600 mg/L $H_2S$ |
| Fe | 0.22 | 0.56 | |
| Cl | 11,510 | 12,400 | |
| $SO_4$ | 2,930 | 1,310 | |
| $NO_3$ | 2,810 | 0 | |
| $NO_2$ | 0 | 0 | |
| F | 121 | 13 | |
| pH | 7.20 | 7.60 | 3.5 |
| Corrosion NACE ID 182 72 h 45° C., mpa | 41.8 | 38.0 | 45.8 |

TABLE 2

Corrosion inhibition efficiencies electrochemically evaluated with EIS using the test water SP1.

| Family | Structure | Concentration mg/L | Inhibition efficiency % |
|---|---|---|---|
| Imidazole | IMC12 | 2500 | 95.4 |
| | | 500 | 80.9 |
| | | 50 | 23.1 |
| | IMC14 | 2500 | 98.0 |
| | | 500 | 78.9 |
| | | 50 | 19.8 |
| | IMC18 | 2500 | 94.4 |
| | | 500 | 84.5 |
| | | 50 | 20.2 |
| Benzotriazole | BZC6 | 2500 | 73.7 |
| | | 500 | 35.3 |
| | | 50 | 18.2 |
| | BZC10 | 2500 | 86.7 |
| | | 500 | 69.1 |
| | | 50 | 10.6 |
| | BZC14 | 2500 | 96.2 |
| | | 500 | 97.4 |
| | | 50 | 55.8 |
| | BZC18 inst | 2500 | 98.6 |
| | | 500 | 96.2 |
| | | 50 | 18.5 |
| Ionic liquids | MIMC4 | 2500 | 76.0 |
| | | 500 | 61.9 |
| | | 50 | 15.2 |
| | MIMC8 | 2500 | 76.2 |
| | | 500 | 58.6 |
| | | 50 | 10.3 |
| | MIMC12 | 2500 | 89.3 |
| | | 500 | 77.7 |
| | | 50 | 12.4 |
| | MIMC16 | 2500 | 83.1 |
| | | 500 | 76.5 |
| | | 50 | 20.3 |

Example 8

Evaluation of Corrosion Inhibition Properties of Binary Formulations

Preparation of Binary Formulations

In order to improve the corrosion inhibition efficiency that individually shows the structures at lower dosages, the following formulations between members of the same family and two different families were prepared:

Family IC12C14, wherein component A1 is N-[1H-imidazole-(4-methylidene)]-dodecane-1-amine, whereas the component A2 is N-[1H-imidazole-(4-methylidene)]-tetradecane-1-amine.

Ratio 1:0 Is prepared weighing 100 g of component A1 and adding 67 mL of xylene, is moderately stirred to get full integration.

Ratio 3:1 Is prepared weighing 75 g of A1, 67 mL of xylene are added whereas it is moderately stirred, 25 g of component A2 are added and stirring is continued to get full integration.

Ratio 1:1 50 g of A1 and 50 g of A2 are weighed, the preparation is similar to the last one.

Ratio 1:3 25 g of A1 and 75 g of A2 are weighed, the preparation is similar to the last one.

Ratio 0:1 100 g of A2 are weighed, the preparation is similar to the ratio 1:0.

Family BZC6C12, wherein component B1 is N-(1H-benzotriazole-1-methyl)-hexane-1-amine, whereas the component B2 is N-(1H-benzotriazole-1-methyl)-dodecane-1-amine.

The same ratio as those of family A are prepared, weighing in this case the same quantities but of the compounds B1 and B2 using methanol as solvent.

Family MIMC4C18, wherein component C1 is 1-butyl-3-methylimidazolium bromide, whereas component C2 is 1-octadecyl-3-methylimidazolium bromide.

The same ratio as those of family A are prepared, weighing in this case the same quantities but of the compounds C1 and C2 using toluene as solvent.

Family BZC6MIMC4, wherein component A1 is N-(1H-benzotriazole-1-methyl)-hexane-1-amine, whereas component C1 is 1-butyl-3-methylimidazolium bromide.

The same ratio as those of family A are prepared, weighing in this case the same quantities but of the compounds A1 and C1 using 67 mL of a 50/50 mixture of methanol/toluene as solvent.

Family BZC12MIMC18, wherein component A2 is N-(1H-benzotriazole-1-methyl)-dodecane-1-amine,
whereas component C2 is 1-octadecyl-3-methylimidazolium bromide.

The same ratio as those of family A are prepared, weighing in this case the same quantities but of the compounds A2 and C2 using 67 mL of a 50/50 mixture of methanol/toluene as solvent.

These formulations were evaluated with the same electrochemical methodology described in Example 7 using SP1 test solution and a dose of 50 mg/L of each one of them, the obtained corrosion inhibition results are shown in Table 3.

TABLE 3

Corrosion inhibition efficiencies of binary formulations, electrochemically evaluated with EIS technique using test water SP1 and a dose of 50 mg/L each.

| | | Inhibition efficiency, % | | | | |
|---|---|---|---|---|---|---|
| Family | Formulation | 1:0 | 3:1 | 1:1 | 1:3 | 0:1 |
| Amine Imidazole | IC12C14 | 95.5 | 87.0 | 93.2 | 92.3 | 98.0 |
| Amine Benzotriazole | BZC6C12 | 89.0 | 85.3 | 87.4 | 76.2 | 82.0 |
| Ionic liquid | MIMC4C18 | 76.0 | 50.9 | 70.9 | 92.0 | 83.0 |
| Amine Benzotriazole/ Ionic liquid | BZC6MIMC4 | 89.0 | 91.1 | 90.8 | 92.2 | 76.0 |
| Amine Benzotriazole/ Ionic liquid | BZC12MIMC18 | 82.0 | 84.7 | 81.5 | 84.0 | 83.0 |

Additionally, the formulations were evaluated by the method of the wheel (Wheel test) according to the NACE ID 182 specification using the test solution SP3 and a dosage of 50 ppm. Corrosion inhibition efficiencies obtained with this methodology are presented in Table 4.

TABLE 4

Corrosion inhibition efficiencies of binary formulations, evaluated with the method of the wheel (Wheel test) using test water SP3 and a dosage of 50 mg/L each. 72 hours of test at 45° C.

| | | Inhibition efficiency, % | | | | |
|---|---|---|---|---|---|---|
| Family | Formulation | 1:0 | 3:1 | 1:1 | 1:3 | 0:1 |
| Amine Imidazole | IC12C14 | 71.6 | 85.4 | 83.4 | 87.7 | 81.9 |
| Amine Benzotriazole | BZC6C12 | 82.7 | 82.9 | 91.4 | 90.4 | 59.9 |
| Methyl-imidazolium | MIMC4C18 | 84.2 | 85.9 | 87.3 | 93.2 | 82.3 |
| Amine Benzotriazole/ Methyl-imidazolium | BZC6MIMC4 | 82.7 | 81.6 | 87.0 | 86.7 | 84.2 |
| Amine Benzotriazole/ Methyl-imidazolium | BZC12MIMC18 | 59.9 | 79.8 | 82.2 | 84.5 | 90.3 |

Example 9

Evaluation of Corrosion Inhibition Properties of Ternary Formulations

Preparation of Ternary Formulations

Formulations of three components are prepared, wherein all components may belong to different families, or two of them belong to the same family whereas the other belong to another family.

Family IC12BZC6MIMC4, wherein the component A1 is N-[1H-imidazole-(4-methylidene)]-dodecane-1-amine; the component B1 is N-(1H-benzotriazole-1-methyl)-hexane-1-amine; and the component C1 is 1-butyl-3-methylimidazolium bromide.

In order to prepare the 1:1:1 ratio, 33.3 g of A1 are weighed and 22 mL of xylene are added; at moderate stirring, 33.3 g of B1 is added and stirring is continued adding 22 mL of methanol; finally, and maintaining stirring, 33.3 3 of C1 and 34 mL of toluene are added, stirring is continued up to complete integration.

Family IC14BZC12MIMC18, wherein component A2 is N-[1H-imidazole-(4-methylidene)]-tetradecane-1-amine; the component B2 is N-(1H-benzotriazole-1-methyl)-dodecane-1-amine; and component C2 is 1-octadecyl-3-methyl-imidazolium bromide.

The procedure of the above formulation is followed but using components A2, B2 and C2.

Family BZC6C12MIMC4, wherein component B1 is N-(1H-benzotriazole-1-methyl)-hexane-1-amine; component B2 is N-(1H-benzotriazole-1-methyl)-dodecane-1-amine; and component C1 is 1-butyl-3-methylimidazolium bromide.

The same procedure of the above formulation is followed but using components B1, B2 and C1 and methanol as solvent to solubilize compounds B and toluene.

Family BZC6C12IC14, wherein component B1 is N-(1H-benzotriazole-1-methyl)-hexane-1-amine; component B2 is N-(1H-benzotriazole-1-methyl)-dodecane-1-amine; A2 is N-[1H-imidazole-(4-methylidene)]-tetradecane-1-amine.

The procedure of the above formulation is followed but using components B1, B2 and C2.

Family IC12C14BZC12, wherein component A1 is N-[1H-imidazole-(4-methylidene)]-dodecane-1-amine; component A2 is N-[1H-imidazole-(4-methylidene)]-tetradecane-1-amine; and component B2 is N-(1H-benzotriazole-1-methyl)-dodecane-1-amine.

The procedure of the above formulation is followed but using components A1, A2 and B2 and xylene to solubilize compounds A and methanol as solvents.

Family 1C12C14M1MC18, wherein component A1 is N-[1H-imidazole-(4-methylidene)]-dodecane-1-amine; component A2 is N-[1H-imidazole-(4-methylidene)]-tetradecane-1-amine; and component C2 is 1-octadecyl-3-methylimidazolium bromide.

The procedure of the above formulation is followed but using components A1, A2 and C2 and xylene to solubilize compounds A and toluene as solvents.

The evaluation of the corrosion inhibition efficiency, using a dosage of 50 mg/L of these formulations in various behavioral tests and with different media is shown in Table 5.

TABLE 5

Corrosion inhibition efficiencies of ternary formulations evaluated with test methods: rotating cylinder, wheel (Wheel test) and Electrochemical (EIS) using test solutions SP1, SP2 and SP3, as indicated, and a dosage of 50 mg/L of each formulation.

| | % of corrosion inhibition efficiency | | | | | |
|---|---|---|---|---|---|---|
| | Rotating cylinder ASTM G 185 Medium: SP1 | | Method of the wheel NACE ID 182 | | | EIS Medium: SP3 |
| Formulation | Weight loss | Rp | SP1 | SP2 | SP3 | |
| IC12BZC6MIMC4 | 90.8 | 96.3 | 95.9 | 96.6 | 93.6 | 99.9 |
| IC14BZC12MIMC18 | 93.5 | 94.7 | 97.3 | 95.2 | 96.1 | 98.9 |
| BZC6C12MIMC4 | 96.7 | 90.5 | 93.2 | 90.9 | 91.7 | 97.2 |
| BZC6C12IC14 | 91.1 | 96.1 | 92.9 | 94.3 | 95.0 | 99.0 |
| IC12C14BZC12 | 95.8 | 96.5 | 91.4 | 92.6 | 93.3 | 98.3 |
| IC12C14MIMC18 | 93.1 | 92.0 | 90.4 | 95.4 | 94.5 | 99.7 |

What is claimed is:

1. A corrosion inhibiting composition for inhibiting corrosion of metal surfaces in contact with crude oil, said corrosion inhibiting composition comprising crude oil and a mixture of at least two different corrosion inhibiting compounds and an organic solvent, said corrosion inhibiting compounds selected from the group consisting of imidazoles and benzotriazoles, said imidazoles having the formula:

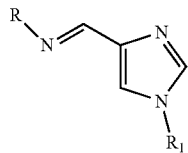

wherein R is a linear or branched, saturated or unsaturated hydrophobic hydrocarbon chain containing 2 to 25 carbon atoms; and $R_1$ is hydrogen or a linear or branched alkyl radical containing from 1 to 5 carbon atoms; and
said benzotriazoles having the formula:

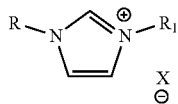

wherein R is a linear or branched, saturated or unsaturated hydrophobic hydrocarbon chain containing 2 to 25 carbon atoms.

2. The corrosion inhibiting composition of claim 1, further comprising an ionic liquid having the formula

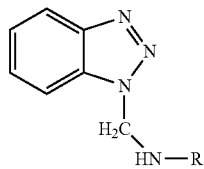

where R is a linear or branched, saturated or unsaturated hydrophobic hydrocarbon chain containing 2 to 25 carbon atoms; and $R_1$ is hydrogen or a linear or branched alkyl radical containing from 1 to 5 carbon atoms, and X is Cl, Br or I.

3. The corrosion inhibiting composition of claim 2, wherein said composition comprises said imidazole, benzotriazole, and ionic liquid in a molar ratio selected from the group consisting of 1:1:1, 2:1:1, 1:2:1, and 1:1:2.

4. The corrosion inhibiting composition of claim 1, wherein said organic solvent is selected from the group consisting of an alcohol, xylene, toluene and mixtures thereof.

5. The corrosion inhibiting composition of claim 3, wherein said alcohol is methanol.

6. The corrosion inhibiting composition of claim 1, wherein said composition comprises said mixture of said imidazole and said benzotriazole in a molar ratio of 1:3 to 3:1.

7. The corrosion inhibiting composition of claim 1, wherein said crude oil contains 0.4 to 40% by wt. water, 10,000 to 70,000 ppm inorganic salts, and dissolved $H_2S$ and oxygen.

8. The corrosion inhibiting composition of claim 1, wherein said mixture is selected from the group consisting of;

a first imidazole where R is a saturated or unsaturated hydrophobic $C_2$ to $C_{10}$ hydrocarbon $R_1$ is H or a linear or branched alkyl $C_1$ to $C_5$ hydrocarbon, and a second imidazole where R is a saturated or unsaturated hydrophobic $C_{11-25}$ hydrocarbon, and $R_1$ is H or a linear or branched alkyl $C_1$ to $C_5$ hydrocarbon; and
a first benzotriazole where R is a saturated or unsaturated hydrophobic $C_2$ to $C_{10}$ hydrocarbon, and a second benzotriazole where R is a saturated or unsaturated hydrophobic $C_{11}$ to $C_{25}$ hydrocarbon.

9. The corrosion inhibiting composition of claim 1, wherein said crude oil includes said mixture of said at least two corrosion inhibiting compounds in an amount of 500 to 2500 mg/L.

10. A corrosion inhibitng composition for inhibiting corrosion of metal surfaces in contact with crude oil, wherein said corrosion inhibiting composition comprises an organic solvent and a mixture of corrosion inhibiting compounds selected from the group consisting of;
at least one imidazole and at least one benzotriazoles;
at least one imidazole and at least one ionic liquid;
at least one benzotriazole and at least one ionic liquid; and
at least one imidazole, at least one benzotriazole, and at least one ionic liquid,
wherein said at least one ionic liquid has the formula

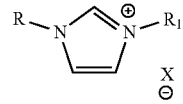

where R is a linear or branched saturated or unsaturated hydrophobic hydrocarbon chain containing 2 to 25 carbon atoms; and $R_1$ is hydrogen or a linear or branched alkyl radical containing from 1 to 5 carbon atoms, and X is Cl, Br or I,
said at least one imidazole has the formula:

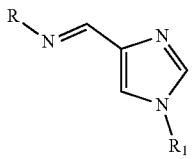

wherein R is a linear or branched, saturated or unsaturated hydrophobic hydrocarbon chain containing 2 to 25 carbon atoms; and $R_1$ is hydrogen or a linear or branched alkyl radical containing from 1 to 5 carbon atoms; and
said at least one benzotriazole has the formula:

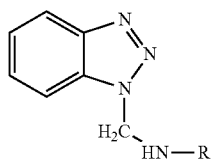

wherein R is a linear or branched, saturated or unsaturated hydrophobic hydrocarbon chain containing 2 to 25 carbon atoms.

11. The corrosion inhibiting composition of claim 10, wherein said corrosion inhibiting composition further comprises crude oil having a water concentration from 0.2 to 40% by weight; a salt concentration of 10,000 to 70,000 ppm and hydrogen sulfide concentration from 0 and 600 ppm.

12. The corrosion inhibiting composition of claim 11, wherein said corrosion inhibiting composition includes said corrosion inhibiting compounds in an amount of 500 to 2500 mg/L based on the amount of the crude oil.

13. The corrosion inhibiting composition of claim 10, where said mixture comprises a first imidazole where R is a saturated or unsaturated hydrophobic $C_2$ to $C_{10}$ hydrocarbon and a second imidazole where R is a saturated or unsaturated hydrophobic $C_{11}$ to $C_{25}$ hydrocarbon.

14. The corrosion inhibiting composition of claim 10, where said mixture comprises a first benzotriazole where R is a saturated or unsaturated hydrophobic $C_2$ to $C_{10}$ hydrocarbon, and a second benzotriazole where R is a saturated or unsaturated hydrophobic $C_{11}$ to $C_{25}$ hydrocarbon.

15. The corrosion inhibiting composition of claim 10, wherein said at least one ionic liquid comprises a first ionic liquid where R is a saturated or unsaturated hydrophobic $C_2$ to $C_{10}$ hydrocarbon, and a second ionic liquid where R is a $C_{11}$ to $C_{25}$ hydrocarbon.

16. The corrosion inhibiting composition of claim 10, wherein said mixture comprises a first imidazole where R is a saturated or unsaturated hydrophobic $C_{11}$ to $C_{25}$ hydrocarbon, and a first benzotriazole where R is a saturated or unsaturated hydrophobic $C_2$ to $C_{11}$ hydrocarbon.

17. The corrosion inhibiting composition of claim 10, wherein said mixture comprises said at least one imidazole where R is a saturated or unsaturated hydrophobic $C_{11}$ to $C_{25}$ hydrocarbon, and said at least one ionic liquid where R is a linear or branched, saturated or unsaturated hydrophobic $C_{11}$ to $C_{25}$ hydrocarbon.

18. The corrosion inhibiting composition of claim 10, wherein said mixture comprises said at least one benzotriazole where R is a saturated or unsaturated hydrophobic $C_{11}$ to $C_{25}$ hydrocarbon, and said at least one ionic liquid where R is a linear or branched saturated or unsaturated hydrophobic $C_{11}$ to $C_{25}$ hydrocarbon.

19. The corrosion inhibiting composition of claim 10, wherein said mixture is selected from the group consisting of
a mixture of a first imidazole where R is a saturated or unsaturated hydrophobic $C_2$ to $C_{10}$ hydrocarbon, a second imidazole where R is a saturated or unsaturated hydrophobic $C_{11}$ to $C_{25}$ hydrocarbon, and said ionic liquid where R is a linear or branched saturated or unsaturated hydrophobic $C_2$ to $C_{10}$ hydrocarbon;
a mixture of a first imidazole where R is a saturated or unsaturated hydrophobic $C_2$ to $C_{10}$ hydrocarbon, a second imidazole where R is a saturated or unsaturated hydrophobic $C_{11}$ to $C_{25}$ hydrocarbon, and said ionic liquid where R is a linear or branched saturated or unsaturated hydrophobic $C_{11}$ to $C_{25}$ hydrocarbon;
a mixture of a first benzotriazole where R is a saturated or unsaturated hydrophobic $C_2$ to $C_{10}$ hydrocarbon, a second benzotriazole where R is a saturated or unsaturated hydrophobic $C_{11}$ to $C_{25}$ hydrocarbon, and said ionic liquid where R is a linear or branched saturated or unsaturated hydrophobic to $C_{10}$ hydrocarbon; and
a mixture of a first benzotriazole where R is a saturated or unsaturated hydrophobic $C_2$ to $C_{10}$ hydrocarbon, a second benzotriazole where R is a saturated or unsaturated hydrophobic $C_{11}$ to $C_{25}$ hydrocarbon and said ionic liquid where R is a linear or branched saturated or unsaturated hydrophobic $C_{11}$ to $C_{25}$ hydrocarbon.

20. The corrosion inhibiting composition of claim 10, where said composition comprises a mixture of said imidazole, benzotriazole, and ionic liquid in a molar ratio selected from the group consisting of 1:1:1; 2:1:1, 1:2:1, and 1:1:2.

21. A method of producing a corrosion inhibiting composition comprising,
providing a mixture of corrosion inhibiting compounds selected from the group consisting of:
at least one imidazole and at least one benzotriazole;
at least one imidazole and at least one ionice liquid;
at least one benzotriazole and at least one ionic liquid; and
at least one imidazole , at least one benzotriazole, and at least one ionice liquid,
wherein said at least one imidazole has the formula

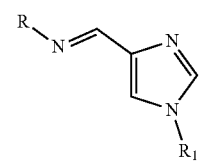

wherein R is a linear branched, saturated or unsaturated hydrophobic hdrocarbon chain containing 2 to 25 carbon atoms; and
said at least one benzotriazole has the formula:

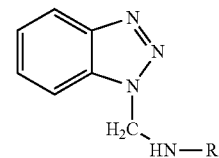

wherein R is a linear or branched, saturated or unsaturated hydrophobic hydrocarbon chaim containing 2 to 25 carbom atoms, and
said at least one ionic fluid has the formula

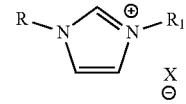

where R is a linear or branched saturated or unsaturated hydrophobic hydrocarbon chain containing 2 to 25 carbon atoms; and $R_1$ is hydrogen or a linear branched alkyl radical containing 1 to 5 carbon atoms and X is Cl, Br or I,
mixing the mixture of corrosion inhibiting compounds and organic solvent in crude oil, where said corrosion inhibiting compounds are included in an amount of 500 to 2500 mg/l based on the amount of crude oil.

* * * * *